United States Patent
Kurdikar et al.

[11] Patent Number: 6,087,471
[45] Date of Patent: Jul. 11, 2000

[54] HIGH TEMPERATURE PHA EXTRACTION USING PHA-POOR SOLVENTS

[75] Inventors: Devdatt L. Kurdikar, Maryland Heights; Fred E. Strauser, St. Charles; A. John Solodar, University City; Mark D. Paster, Chesterfield, all of Mo.

[73] Assignee: Monsanto Company, St. Louis, Mo.

[21] Appl. No.: 09/060,120

[22] Filed: Apr. 14, 1998

Related U.S. Application Data

[60] Provisional application No. 60/043,018, Apr. 15, 1997.

[51] Int. Cl.⁷ ....................................................... C08F 6/00
[52] U.S. Cl. ............................................. 528/480; 528/480
[58] Field of Search ................................... 528/480, 491; 435/135

[56] References Cited

U.S. PATENT DOCUMENTS

| | | | |
|---|---|---|---|
| 4,205,162 | 5/1980 | Herscovici | 528/499 |
| 4,562,245 | 12/1985 | Stageman | 528/361 |
| 4,705,604 | 11/1987 | Vanlautem et al. | 203/67 |
| 4,968,611 | 11/1990 | Transsnig et al. | 435/135 |
| 5,213,976 | 5/1993 | Blauhut et al. | 435/135 |
| 5,422,257 | 6/1995 | Ohleyer | 435/135 |
| 5,478,921 | 12/1995 | Roby et al. | 528/480 |
| 5,496,923 | 3/1996 | Suizu et al. | 528/501 |
| 5,536,419 | 7/1996 | Esalona et al. | 210/767 |

FOREIGN PATENT DOCUMENTS

| | | | |
|---|---|---|---|
| 9302312 | 2/1995 | Brazil | C12P 7/62 |
| 0 058 480 | 8/1982 | European Pat. Off. | C12P 7/62 |
| 0 124 309 | 11/1984 | European Pat. Off. | C12P 7/62 |
| 0 452 111 | 10/1991 | European Pat. Off. | C08G 63/90 |
| 0 707 024 | 4/1996 | European Pat. Off. | C08G 63/90 |
| 2 338 291 | 8/1977 | France | C08F 63/06 |
| 1 568 719 | 6/1980 | United Kingdom | C08G 63/72 |
| 2 120 671 | 12/1983 | United Kingdom | C08G 63/72 |
| 94/10289 | 5/1984 | WIPO | C12N 1/08 |
| 95/33064 | 12/1995 | WIPO | C12P 7/62 |
| 95/33065 | 12/1995 | WIPO | C12P 7/62 |
| 96/06178 | 2/1996 | WIPO | C12P 7/62 |
| 96/06179 | 2/1996 | WIPO | C12P 7/62 |
| 96/25452 | 8/1996 | WIPO | C08J 3/03 |
| 97/07229 | 2/1997 | WIPO | C12P 7/62 |
| 97/07230 | 2/1997 | WIPO | C12P 7/62 |
| 97/08931 | 3/1997 | WIPO | |
| 97/15681 | 5/1997 | WIPO | C12P 7/62 |

*Primary Examiner*—Terressa M. Boykin
*Attorney, Agent, or Firm*—Jon H. Beusen, Esq.; Howrey Simon; Arnold & White LLP

[57] ABSTRACT

Polyhydroxyalkanoate (PHA) polyester is extracted from biomass by dissolving the PHA in a non-halogenated solvent which comprises a PHA-poor solvent that dissolves less than 1% of the PHA at temperatures less than the solvent boiling point, or a mixture of a PHA-poor solvent and a PHA-good solvent. Following extraction of PHA under pressure at a temperature above about 80° C., typically above the boiling point of the PHA-poor solvent, PHA polymer is precipitated by cooling the PHA-enriched solvent mixture. Suitable PHA-poor solvents can include linear and branched $R_1$—OH alcohols and $R_2$—$COOR_3$ esters where $R_1=C_1-C_4$, $R_2=$H, $C_1, C_2$, or $C_3$, and $R_3=C_1-C_5$.

20 Claims, No Drawings

HIGH TEMPERATURE PHA EXTRACTION USING PHA-POOR SOLVENTS

This application is based on Provisional Application Ser. No. 60/043,018, filed Apr. 15, 1997.

BACKGROUND OF THE INVENTION

This invention relates to a process for the extraction and recovery of polyhydroxyalkanoate (PHA) from biomass.

There has been considerable interest in recent years in the use of biodegradable polymers to address concerns over plastic waste accumulation. The potential worldwide market for biodegradable polymers is enormous. Some of the markets and applications most amenable to the use of such biopolymers involve those having single, short use applications, including packaging, personal hygiene, garbage bags, and others. These applications, although poorly suited for recycling, are ideally suited for biodegradation through composting.

PHA biopolymers are thermoplastic polyesters produced by numerous microorganisms in response to nutrient limitation. The commercial potential for PHA spans many industries, and is derived primarily from certain advantageous properties which distinguish PHA polymers from petrochemical-derived polymers, namely excellent biodegradability and natural renewability. The success of PHA as a viable alternative to petrochemical-derived polymers, however, will depend upon the design and implementation of efficient and selective means of PHA production and recovery.

An improved understanding of the biology of PHA biosynthetic pathways has allowed for the use of microbial organisms, both natural and recombinant, and more recently plant cells, to produce significant quantities of PHA. Although such approaches have identified promising routes to PHA production, there remain obstacles to efficient and cost-effective PHA recovery from source materials at a useful level of quality and purity. Much of the effort directed to identifying methods for recovery of PHA have focused on recovery from bacterial sources using halogenated hydrocarbon solvents. The environmental implications and human toxicities associated with halogenated compounds, however, have created a need for separation processes which utilize PHA solvents with more benign properties.

SUMMARY OF THE INVENTION

In accordance with one aspect of the present invention, there is provided a method of recovering PHA from biomass comprising:

providing biomass containing PHA;

dissolving the PHA with an effective PHA-poor solvent typically at a temperature above the boiling point of the PHA-poor solvent to produce PHA-enriched solvent and residual biomass materials;

separating the residual biomass materials from the PHA-enriched solvent;

reducing the temperature of the PHA-enriched solvent such that PHA precipitation occurs; and recovering the precipitated PHA polymer.

An effective PHA-poor solvent comprises a non-halogenated solvent which preferably dissolves less than about 1% (w/v) of the PHA being extracted at a temperature less than the solvent boiling point. Suitable PHA-poor solvents can be selected from the group consisting of linear and branched $R_1$—OH alcohols and $R_2$—$COOR_3$ esters where $R_1=C_1-C_4$, $R_2=H$ or $C_1-C_3$, and $R_3=C_1-C_5$. Examples of preferred PHA-poor solvents include methanol, ethanol, n-propanol, iso-propanol, and n-butanol.

In accordance with a further aspect of the present invention, PHA is dissolved with a solvent mixture comprising a PHA-good solvent and a PHA-poor solvent at a temperature effective for dissolving the PHA, typically at a temperature above about 80° C. The PHA is then precipitated by reducing the temperature of the PHA-enriched solvent.

Suitable PHA-good solvents for use in this aspect of the invention can include essentially any solvent effective for solubilizing the PHA of interest. Preferred PHA-good solvents are typically selected from the group consisting of cyclic and acyclic (linear and branched) $R'$—OH alcohols where $R'=C_4-C_{10}$, cyclic and acyclic $R''$—$COOR'''$ esters where $R''=H$ or $C_1-C_6$ and $R'''=C_1-C_7$, cyclic and acyclic $R''$—$COOR'''$ esters where $R'=H$ or $C_1-C_6$ and $R'''=C_1-C_7$ and wherein at least one oxygen is substituted for at least one carbon in $R''$ or $R'''$, cyclic and acyclic $R^1$—CON—$(R^2)_2$ amides where $R^1=H$ or $C_1-C_6$ and $R^2=C_1-C_6$, and cyclic and acyclic $R^3$—CO—$R^4$ ketones where $R^3=C_1-C_6$ and $R^4=C_1-C_6$.

Examples of preferred PHA-good solvents for use in the methods of the present invention include butyl acetate, isobutyl acetate, ethyl lactate, isoamyl acetate, benzyl acetate, 2-methoxy ethyl acetate, tetrahydrofurfuryl acetate, methyl propionate, propyl propionate, butyl propionate, pentyl propionate, butyl butyrate, isobutyl isobutyrate, ethyl butyrate, ethyl valerate, methyl valerate, benzyl benzoate, methyl benzoate, dimethyl succinate, dimethyl glutarate, dimethyl adipate, isobutyl alcohol, 1-butanol, 2-methyl-1-butanol, 3-methyl-1 butanol, 1-pentanol, 3-pentanol, amyl alcohol, allyl alcohol, hexanol, heptanol, octanol, cyclohexanol, 2-ethylhexanol, tetrahydrofurfuryl alcohol, furfuryl alcohol, benzyl alcohol, 2-furaldehyde, methyl isobutyl ketone, methyl ethyl ketone, g-butyrolactone, methyl n-amyl ketone, 5-methyl-2-hexanone, ethyl benzene, 1,3-dimethoxybenzene, cumene, benzaldehyde, 1,2-propanediol, 1,2-diaminopropane, ethylene glycol diethyl ether, 1,2,3-trimethylbenzene, 1,2,4-trimethylbenzene, 1,3-dioxane, 1,4-dioxane, 1-nitropropane, toluene-2,4-diisocyanate, acetic acid, acrylic acid, acetic anhydride, alpha-methylstyrene, acetophenone, toluene, ethylene glycol diacetate, dimethylsulfoxide and propylene carbonate, dimethyl acetamide, dimethyl formamide, or mixtures thereof.

DESCRIPTION OF ILLUSTRATIVE EMBODIMENTS

The embodiments disclosed herein relate to novel methods for the recovery of PHA polymers from biomass materials, wherein the biomass materials are derived from PHA-producing plants or PHA-producing microorganisms. The methods are applicable to the recovery of essentially any type of PHA polymer produced by plant or microbial organisms either naturally or through genetic engineering PHA is a polymer made from repeating units having the following general structure:

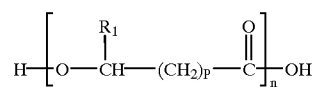

wherein $R_1$ is preferably an H, alkyl, or alkenyl; p is 0, 1, 2, or 3; and n is an integer. PHA can consist entirely of a single monomeric repeating unit, in which case it is referred to as a homopolymer. For example, polyhydroxybutyrate (PHB) homopolymer has repeating monomeric units wherein $R_1=C_1$ alkyl, and p=1. Copolymers, in contrast, contain two different types of monomeric repeating units. Polyhydroxybutyrate-co-hydroxyvalerate (PHBV) copolymer contains one type of monomer unit where $R_1=C_1$ alkyl and p=1, and a second type of monomer unit where $R_1=C_2$ alkyl, and p=1. Another copolymer of interest contains 3-hydroxybutyrate and 4-hydroxybutyrate units (P3HB4HB). When three different types of repeating units are present the polymer is referred to as a terpolymer.

The methods disclosed herein are also be applicable to the recovery of PHA which has been modified in a plant or microbial organism to provide improved or beneficial properties. In particular, the methods are useful for the extraction and recovery of PHAs modified to contain hydroxy-terminated end groups. Hydroxyterminated PHAs are useful in the production of graft, random and block polymers and copolymers with unique and improved properties, as disclosed in U.S. provisional application 60\044,042, filed Apr. 21, 1997.

Particularly preferred PHA polymers to be recovered according to this invention include poly(hydroxybutyrate-co-hydroxyvalerate) (PHBV) copolymers, poly(3-hydroxybutyrate-co-4-hydroxybutyrate) (P3HB4HB) copolymers, and hydroxyterminated polymers and copolymers of polyhydoxybutyrate (PHB-OH).

The invention is applicable to PHA recovery from essentially any plant type. The plants can be monocots or dicots. Suitable plant source materials from which PHA can be recovered include roots, stems, leaves, flowers, fruits, seeds, etc. In one preferred embodiment, the biomass source is corn stover, switchgrass, sugarcane. The invention is also well suited for PHA recovery from oil-bearing seeds. For oilseed crops, such as canola, rapeseed, soybean, safflower, and sunflower, genetic engineering can result in PHA being biosynthetically produced in the seeds of the crops. In order to recover PHA polymer from the seeds, it is necessary to separate the polymer from the vegetable oil and oilseed meal also present. The seeds are typically processed by conventional methods. For example, they can be crushed and/or dehulled and/or oil-extracted and/or protein extracted prior to PHA extraction, although not necessarily in this order. The oilseed meal which is separated from the PHA-enriched solvent may be further processed and utilized as animal feed, or, utilized as an additive in animal feed.

It has been found that non-halogenated PHA-poor solvents are effective for dissolving PHAs when extraction is performed under pressure at high temperatures. This allows for the simple and efficient recovery of PHA by extracting the polymer under pressure at a temperature above the boiling point of the PHA-poor solvent, and then precipitating the PHA by reducing the temperature of the PHA-enriched solvent. Typically, the temperature is reduced to below the boiling point of the PHA-poor solvent. If desired, the color and quality of the recovered PHA may be improved, for example, by washing the PHA before drying.

One advantage of this approach relates to the ease with which PHA can be recovered. Upon cooling of the PHA-enriched solvent mixture, a precipitate typically forms which is easily removed from the solvent. In contrast, other solvent systems used for PHA extraction which involve subsequent recovery of PHA by temperature reduction generally result in a PHA-enriched solvent which forms a stable gel upon cooling. Additional steps are then required in order to separate PHA polymer from the gel. For example, the gels are often compressed into flakes, and remaining solvent present in the flakes is removed by heat evaporation. Optimal prevention of gel formation when practicing the methods of this invention may depend on the the polymer content (i.e., wt. percent) present in the solvent and to some extent on the particular solvent used. Routine optimization will readily identify the desired conditions for a given polymer-solvent combination.

Other polymer recovery approaches require the use of precipitation solvents to precipitate PHA from a PHA-enriched solvent. The present invention is advantageous in providing methods for the recovery of PHA polymer without undesirable gel formation and without the requirement for precipitation solvents by extracting PHA at high temperatures, under pressure, using the solvents provided herein, and subsequently cooling the PHA-enriched solvent.

Suitable PHA-poor solvents for use in this invention include $R_1$—OH alcohols and $R_2$—$COOR_3$ esters where $R_1=C_1-C_4$, $R_2$=H or $C_1-C_3$, and $R_3=C_1-C_5$, or other non-halogenated solvents which dissolve less than about 1% w/v (i.e. 1 g PHA in 100 cc solvent) of PHA at temperatures below their boiling points. Preferred PHA-poor solvents include methanol, ethanol, n-propanol, iso-propanol, and n-butanol. A single PHA-poor solvent, or a mixture of PHA-poor solvents, can be used. After PHA recovery, the PHA-poor solvent(s) can be recycled, optionally after purification.

In another embodiment of the present invention, the PHA can be dissolved with a solvent mixture which comprises a PHA-good solvent and a PHA-poor solvent at a temperature effective for dissolving the PHA, typically at a temperature above about 80° C. The PHA-good solvent can be selected from essentially any solvent capable of solubilizing the PHA. A 50—50 vol.% mixture of a PHA-good solvent and PHA-poor solvent is known to be effective, however other suitable ratios can be readily determined by the skilled individual and are considered within the scope of this invention. The inclusion of a PHA-good solvent with the PHA-poor solvent has the advantage of reducing the pressure requirements to prevent boiling, yet still allows for the effective precipitation of PHA polymer upon cooling.

Particularly useful as PHA-good solvents are cyclic and acyclic (linear and branched) R'—OH alcohols where $R'=C_4-C_{10}$, cyclic and acyclic R"—COR'" esters where R"=H or $C_1-C_6$ and $R'''=C_1-C_7$, cyclic and acyclic R"—COOR'" esters where R"=H or $C_1-C_6$ and $R'''=C_1-C_7$ and wherein at least one oxygen is substituted for at least one carbon in R" or R'", cyclic and acyclic $R^1$—CON—$(R^2)_2$ amides where $R^1$=H or $C_1-C_6$ and $R^2=C_1-C_6$, and cyclic and acyclic $R^3$—CO—$R^4$ ketones where $R^3=C_1-C_6$ and $R^4=C_1-C_6$.

The following is a representation, not intended to be limiting, of preferred PHA-good solvents for use in the methods of the present invention: butyl acetate, isobutyl acetate, ethyl lactate, isoamyl acetate, benzyl acetate, 2-methoxy ethyl acetate, tetrahydrofurfuryl acetate, methyl propionate, propyl propionate, butyl propionate, pentyl propionate, butyl butyrate, isobutyl isobutyrate, ethyl butyrate, ethyl valerate, methyl valerate, benzyl benzoate, methyl benzoate, dimethyl succinate, dimethyl glutarate, dimethyl adipate, isobutyl alcohol, 1-butanol, 2-methyl-1-butanol, 3-methyl-1 butanol, 1-pentanol, 3-pentanol, amyl alcohol, allyl alcohol, hexanol, heptanol, octanol, cyclohexanol, 2-ethylhexanol, tetrahydrofurfuryl alcohol, furfuryl alcohol, benzyl alcohol, 2-furaldehyde, methyl isobutyl ketone, methyl ethyl ketone, g-butyrolactone, methyl n-amyl ketone, 5-methyl-2-hexanone, ethyl benzene, 1,3-dimethoxybenzene, cumene, benzaldehyde, 1,2-propanediol, 1,2-diaminopropane, ethylene glycol diethyl ether, 1,2,3-trimethylbenzene, 1,2,4- trimethylbenzene, 1,3-dioxane, 1,4-dioxane, 1-nitropropane, toluene-2,4-diisocyanate, acetic acid, acrylic acid, acetic anhydride, alpha-methylstyrene, acetophenone, toluene, ethylene glycol diacetate, dimethylsulfoxide and propylene carbonate, dimethyl acetamide, dimethyl formamide, or mixtures thereof.

It should be noted that PHA composition and morphology (polarity, presence or absence of crystallinity etc.) are determinants of polymer solubility characteristics. Generally, polymers with high crystallinity are more difficult to dissolve than those with low crystallinity. Furthermore, the thermal history of the polymer may also effect solubility. If the PHA has side chains, as the size of the chain increases the number of methylene groups in the polymer increases and therefore the polarity of the polymer changes. However, with a change in the size of the side chains, the crystallinity of the polymer is also effected which in turn effects the solubility characteristics. Such variables make it difficult to accurately predict PHA solubility from simple criteria, such as similarities in chemical architecture or matching of refractive indices, dielectric constants or solubility parameters.

The PHA concentration in the PHA-enriched solvent is typically between 1% and 40% w/v.

After PHA recovery, the PHA-poor solvent(s) and the PHA-good solvent(s) can be recycled, optionally after purification.

The following examples are included to demonstrate preferred embodiments of the invention. It should be appreciated by those of skill in the art that the techniques disclosed in the examples which follow represent discoveries by the inventors which function effectively in the practice of the invention, and thus can be considered to constitute examples of preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

2.015 g of a mixture containing 75% dry canola meal and 25% PHBV (10% HV) was placed in a Soxhlet extraction thimble, which was then placed in a Fisher-Porter (FP) bottle containing 20 cc of methanol so that the thimble was suspended in the liquid. The FP assembly was heated using an oil bath, and the temperature of the methanol as well as the pressure in the FP bottle was measured. Under pressure, when the temperature of the methanol had reached around 121° C., the extraction thimble containing the undissolved meal and the PHA was raised so that it no longer contacted the methanol which contained the dissolved PHA. The polymer solution was then cooled to precipitate PHA in powder form, which was recovered by filtration, washed with water in the filter, and dried in a vacuum oven overnight at 50° C. The color of the recovered PHA was off-white.

EXAMPLE 2

4.008 g of a mixture containing 75% dry canola meal and 25% PHBV (10% HV) was placed in a Soxhlet extraction thimble, which was then placed in a Fisher-Porter (FP) bottle containing 20 cc of methanol so that the thimble was suspended in the liquid. The FP assembly was heated using a oil bath, and the temperature of the methanol as well as the pressure in the FP bottle was measured. Under pressure, when the temperature of the methanol had reached around 119° C., the extraction thimble containing the undissolved meal and the PHA was raised so that it no longer contacted the methanol which contained the dissolved PHA. The polymer solution was then cooled upon which the polymer solution formed a gel. This material was washed in 100 cc of deionized water with agitation. Polymer was recovered by filtration and was dried under vacuum overnight at 50° C. The dried polymer was light tan in color.

EXAMPLE 3

0.2 g PHBV (8% HV) was placed in a sealed 8 dram vial with a mixture of 5.0 ml 2-methyl-1-butanol and 5.0 ml absolute ethanol. This mass was heated at 128° C. until all of the polymer had dissolved. The vial was then removed to the hood and placed in a clamp over a magnetic stirring motor. The tiny stir bar in the vial was then stirred vigorously as the system was allowed to air cool. A clean precipitate came out of solution which was then filtered off, washed with 4×0.7 ml ethanol, and dried under vacuum overnight. The recovery was 97.5%.

EXAMPLE 4

4.031 g of a mixture containing 75% dry canola meal and 25% PHBV (10% HV) were placed in a Soxhlet extraction thimble. This extraction thimble was then placed in a Fisher-Porter (FP) bottle containing a mixture of 10 cc of 2-methyl-1-butanol and 10 cc of methanol so that the thimble was suspended in the solvent mixture with the top of the thimble slightly above the liquid level. The FP assembly was heated using an oil bath. The temperature of the mixture, as well as the pressure in the FP bottle were measured. Under pressure, when the temperature of the solvent mixture had reached about 124° C., the extraction thimble was raised so that it no longer contacted the solvent mixture which contained the dissolved PHA. The polymer solution was then cooled and the polymer formed a gel. This was filtered to remove as much solvent as possible. The polymer was then washed by passing water through the filter cake and the filter medium, and dried in a vacuum oven overnight at 50° C. The color of the recovered PHA was tan.

All of the methods disclosed and claimed herein can be made and executed without undue experimentation in light of the present disclosure. While the compositions and methods of this invention have been described in terms of specific embodiments, it will be apparent to those of skill in the art that variations may be applied to the methods and in the steps or in the sequence of steps of the methods described herein without departing from the concept, spirit and scope of the invention. More specifically, it will be apparent that other solvents may be substituted for those described herein while the same or similar results would be achieved. All such similar substitutes and modifications apparent to those skilled in the art are deemed to be within the spirit, scope and concept of the invention as defined by the appended claims.

What is claimed is:

1. A method for recovering PHA from biomass comprising:

providing biomass containing a PHA;

dissolving the PHA with an effective PHA-poor solvent to produce PHA-enriched solvent and residual biomass materials, wherein the dissolving is performed under pressure and at temperatures above the boiling point of the PHA-poor solvent;

separating the residual biomass materials from the PHA-enriched solvent;

reducing the temperature of the PHA-enriched solvent to cause PHA precipitation; and recovering the precipitated PHA polymer.

2. The method of claim 1, wherein an effective PHA poor solvent dissolves less than 1% w/v of the PHA at temperatures less than the solvent boiling point.

3. The method of claim 1, wherein the PHA-poor solvent is selected from the group consisting of linear and branched $R_1$—OH alcohols and $R_2$—$COOR_3$ esters where $R_1=C_1-C_4$, $R_2$=H, $C_1,C_2$, or $C_3$, and $R_3=C_1-C_5$.

4. The method of claim 1, wherein the PHA-poor solvent is selected from the group consisting of methanol, ethanol, n-propanol, iso-propanol, and n-butanol.

5. The method of claim 1, wherein the PHA-poor solvent comprises a mixture of PHA-poor solvents.

6. The method of claim 1, wherein the PHA is dissolved with a solvent mixture comprising a PHA-good solvent and a PHA-poor solvent.

7. The method of claim 6, wherein the PHA-good solvent is selected from the group consisting of cyclic and acyclic R'—OH alcohols where $R'=C_4-C_{10}$, cyclic and acyclic R"—COOR'" esters where R"=H or $C_1-C_6$ and $R'''=C_1-C_7$, cyclic and acyclic R"—COOR'" esters where R"=H or $C_1-C_6$ and $R'''=C_1-C_7$ and wherein at least one oxygen is substituted for at least one carbon in R" or R'", cyclic and acyclic $R^1$—CON—$(R^2)_2$ amides where $R^1$=H or $C_1-C_6$ and $R^2=C_1-C_6$, cyclic and acyclic $R^3$—CO—$R^4$ ketones where $R^3=C_1-C_6$ and $R^4=C_1-C_6$, dimethyl succinate, dimethyl glutarate, dimethyl adipate, allyl alcohol, tetrahydrofurfuryl alcohol, furfuryl alcohol, g-butyrolactone, ethyl benzene, 1,3-dimethoxybenzene, cumene, benzaldehyde, 2-furaldehyde, 1,2-propanediol, 1,2-diaminopropane, ethylene glycol diethyl ether, 1,2,3-trimethylbenzene, 1,2,4-trimethylbenzene, 1,3-dioxane, 1,4-dioxane, 1-nitropropane, toluene-2,4-diisocyanate, acetic acid, acrylic acid, acetic anhydride, alpha-methylstyrene, toluene, ethylene glycol diacetate, dimethyl sulfoxide, and propylene carbonate.

8. The method of claim 6, wherein the PHA-good solvent is selected from the group consisting of butyl acetate, isobutyl acetate, ethyl lactate, isoamyl acetate, benzyl acetate, 2-methoxy ethyl acetate, tetrahydrofurfuryl acetate, methyl propionate, propyl propionate, butyl propionate, pentyl propionate, butyl butyrate, isobutyl isobutyrate, ethyl butyrate, ethyl valerate, methyl valerate, benzyl benzoate, methyl benzoate, dimethyl succinate, dimethyl glutarate, dimethyl adipate, isobutyl alcohol, 1-butanol, 2-methyl-1-butanol, 3-methyl-1 butanol, 1-pentanol, 3-pentanol, amyl alcohol, allyl alcohol, hexanol, heptanol, octanol, cyclohexanol, 2-ethylhexanol, tetrahydrofurfuryl alcohol, furfuryl alcohol, benzyl alcohol, 2-furaldehyde, methyl isobutyl ketone, methyl ethyl ketone, g-butyrolactone, methyl n-amyl ketone, 5-methyl-2-hexanone, ethyl benzene, 1,3-dimethoxybenzene, cumene, benzaldehyde, 1,2-propanediol, 1,2-diaminopropane, ethylene glycol diethyl ether, 1,2,3-trimethylbenzene, 1,2,4-trimethylbenzene, 1,3-dioxane, 1,4-dioxane, 1-nitropropane, toluene-2,4-diisocyanate, acetic acid, acrylic acid, acetic anhydride, alpha-methylstyrene, acetophenone, toluene, ethylene glycol diacetate, dimethylsulfoxide and propylene carbonate, dimethyl acetamide, dimethyl formamide, or mixtures thereof.

9. The method of claim 6, wherein the PHA-good solvent comprises a mixture of PHA-good solvents.

10. The method of claim 6, wherein the PHA poor solvent dissolves less than 1% w/v of the PHA at temperatures less than the solvent boiling point.

11. The method of claim 6, wherein the PHA-poor solvent is selected from the group consisting of linear and branched $R_1$—OH alcohols and $R_2$—$COOR_3$ esters where $R_1=C_1-C_4$, $R_2$=H, $C_1,C_2$, or $C_3$, and $R_3=C_1-C_5$.

12. The method of claim 6, wherein the PHA-poor solvent is selected from the group consisting of methanol, ethanol, n-propanol, iso-propanol, and n-butanol.

13. The method of claim 1 wherein the PHA is selected from the group consisting of poly(hydroxybutyrate-co-hydroxyvalerate), poly(3-hydroxybutyrate-co-4-hydroxybutyrate) and hydroxyterminated polymers and copolymers of polyhydoxybutyrate.

14. The method of claim 1, wherein the biomass is a PHA-producing microorganism.

15. The method of claim 1, wherein the biomass is derived from a plant.

16. The method of claim 1, wherein the biomass is selected from the group consisting of plant stems, leaves, flowers, fruits, seeds, and roots.

17. The method of claim 1, wherein the biomass is corn stover, switch grass or sugar cane.

18. The method of claim 1, wherein the biomass is oil-bearing seeds and wherein seed oil is extracted prior to the PHA dissolving step.

19. The method of claim 18, wherein the seeds are from canola, rapeseed, safflower, soybean, or sunflower.

20. The method of claim 18, wherein prior to dissolving PHA the seeds are processed by conventional methods selected from the group consisting of crushing, dehulling, and protein extracting.

* * * * *